United States Patent
Ye

(10) Patent No.: US 10,835,641 B2
(45) Date of Patent: *Nov. 17, 2020

(54) POROUS MATERIAL AND PREPARATION METHOD THEREOF

(71) Applicant: CHONGQING RUNZE PHARMACEUTICAL CO., LTD., Chongqing (CN)

(72) Inventor: Lei Ye, Chongqing (CN)

(73) Assignee: CHONGQING RUNZE PHARMACEUTICALS CO., LTD., Chongqing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/752,587

(22) PCT Filed: Aug. 15, 2016

(86) PCT No.: PCT/CN2016/095326
§ 371 (c)(1),
(2) Date: Feb. 14, 2018

(87) PCT Pub. No.: WO2017/028770
PCT Pub. Date: Feb. 23, 2017

(65) Prior Publication Data
US 2018/0236138 A1 Aug. 23, 2018

(30) Foreign Application Priority Data
Aug. 18, 2015 (CN) .......................... 2015 1 0505230

(51) Int. Cl.
| | | |
|---|---|---|
| *A61L 27/56* | (2006.01) |
| *A61L 27/04* | (2006.01) |
| *A61L 27/02* | (2006.01) |
| *C22C 1/08* | (2006.01) |
| *B22F 3/11* | (2006.01) |
| *C01B 32/956* | (2017.01) |
| *A61L 27/18* | (2006.01) |
| *A61L 27/20* | (2006.01) |
| *B01D 39/20* | (2006.01) |
| *C22C 1/04* | (2006.01) |
| *C04B 35/565* | (2006.01) |

(52) U.S. Cl.
CPC ............. *A61L 27/56* (2013.01); *A61L 27/025* (2013.01); *A61L 27/04* (2013.01); *A61L 27/047* (2013.01); *A61L 27/18* (2013.01); *A61L 27/20* (2013.01); *B01D 39/2027* (2013.01); *B22F 3/11* (2013.01); *B22F 3/1121* (2013.01); *C01B 32/956* (2017.08); *C22C 1/08* (2013.01); *A61L 2430/02* (2013.01); *B01D 2239/10* (2013.01); *B22F 2301/20* (2013.01); *B22F 2998/10* (2013.01); *B22F 2999/00* (2013.01); *C01P 2006/16* (2013.01); *C04B 35/565* (2013.01); *C22C 1/045* (2013.01); *F01N 2330/06* (2013.01); *F01N 2330/22* (2013.01)

(58) Field of Classification Search
CPC ........ B22F 2201/20; B22F 3/11; A61L 27/56; A61L 27/047; A61L 2430/02; A61L 27/04; A61L 27/02; A61L 27/18; A61L 27/025; A61L 27/20; C22C 1/08; C22C 1/05; B01D 2239/10; B01D 39/2027; C01B 32/956; C01P 2006/16
See application file for complete search history.

(56) References Cited

U.S. PATENT DOCUMENTS

| | | | |
|---|---|---|---|
| 4,923,513 A | 5/1990 | Ducheyne et al. |
| 2011/0262993 A1* | 10/2011 | Backov ................ B82Y 30/00 |
| | | | 435/188 |
| 2011/0313538 A1 | 12/2011 | Oh et al. |
| 2012/0219735 A1 | 8/2012 | Bakker |
| 2014/0107371 A1* | 4/2014 | Bakker ................ C07C 209/36 |
| | | | 558/414 |

FOREIGN PATENT DOCUMENTS

| | | | | |
|---|---|---|---|---|
| CN | 101418392 A | 4/2009 |
| CN | 101660076 A | 3/2010 |
| CN | 102205144 A | 10/2011 |
| CN | 102796896 A | 11/2012 |
| CN | 103463673 A | 12/2013 |
| CN | 103520768 A | 1/2014 |
| CN | 104232972 A | * 12/2014 | ............. A61L 27/56 |
| CN | 104232972 A | 12/2014 |

(Continued)

OTHER PUBLICATIONS

English machine translation of CN-104232972-A made Mar. 31, 2019 (Year: 2019).*

(Continued)

*Primary Examiner* — Michael B. Pallay
(74) *Attorney, Agent, or Firm* — Knobbe, Martens, Olson & Bear LLP

(57) ABSTRACT

A porous material and preparation method thereof is provided. The material includes a material body. The body consists of pore cavities classified according to pore size of material and cavity walls surrounding to form the pore cavities. The lower-level pore cavities are arranged on the cavity walls of the upper-level pore cavities framed by surrounding a three-dimensional space. All the pore cavities are interconnected. The preparation method is: mixing raw powders with pore-forming agent for the smallest-level pore cavities of porous material to formulate slurry; uniformly filling the slurry into polymer material support to form green body and get dried and smashed to obtain mixed grains; uniformly mixing the mixed grains with pore-forming agent for upper-level pore cavities greater than the smallest-level pore cavities of porous material to make compact green body; performing vacuum sintering; performing the conventional follow-up treatment according to the raw materials process of porous material.

4 Claims, 2 Drawing Sheets

(56) References Cited

FOREIGN PATENT DOCUMENTS

| | | |
|---|---|---|
| CN | 104258458 A | 1/2015 |
| CN | 104357700 A | 2/2015 |
| CN | 103462729 B | 6/2016 |

OTHER PUBLICATIONS

C.E.Wen et al. Processing of Biocompatible Porous Ti and Mg. Scripta Materialia. Nov. 19, 2001. pp. 1147-1153 vol. 45 No. 10.
Yuejun Chen. Preparation and Properties of titanium Implants with Three-Dimensional Graded Pore Structure. Southwest Jiaotong University Doctor Degree Dissertation. Feb. 15, 2011.

* cited by examiner

Partial Enlarged View of A

B-B

POROUS MATERIAL AND PREPARATION METHOD THEREOF

CROSS REFERENCE TO RELATED APPLICATIONS

This application is the national phase entry of International Application No. PCT/CN2016/095326, filed on Aug. 15, 2016, which is based upon and claims priority to Chinese Patent Application No. CN2015/10,505,230.8, filed on Aug. 18, 2015, the entire contents of which are incorporated herein by reference.

TECHNICAL FIELD

The present invention relates to a porous material, in particular to a porous material with a multilevel pore structure and a preparation method thereof.

BACKGROUND

The porous material is a kind of multi-purpose engineering material with excellent performance, due to excellent physical and chemical properties. Due to the dual attributes of function and structure, the porous material is widely used in separation, filtration, distribution of gas, catalysis, electrochemical processes, noise reduction, shock absorption, shielding, heat exchange, implantation and other processes in many fields like aerospace, atomic energy, electrochemistry, petrochemical industry, metallurgy, machinery, medicine, environmental protection and construction, etc. The existing porous materials are simple in structure, mostly having single-level uniform pores. The traditional preparation methods include foam dipping method, chemical foaming method, pore-forming agent adding method, organic framework replication method and microsphere sintering method. Take the foam dipping method as an example, patent CN10,279,589.6 A 'Preparation Method of Porous Tantalum Medical Implant Material' disclosed a method including the following steps: preparing a tantalum slurry by mixing a solution prepared by an organic binder and dispersant with tantalum powders, pouring the slurry into an organic foam, dipping until pores of the organic foam are filled with the tantalum slurry, then drying to remove the dispersant in the organic foam in which the tantalum slurry was poured, degreasing under an inert gas protective atmosphere to remove the organic binder and the organic foam, sintering under vacuum to obtain a porous sintered body, cooling the porous sintered body, annealing under vacuum and subjecting to conventional follow-up treatment to obtain the porous tantalum. Chemical foaming method is to mix the materials which generate gas during chemical reaction at high temperature with raw material powders, then processing and foaming at a certain temperature to produce porous materials. Pore-forming agent method is to add a pore-forming agent in the materials, making it volatilized at high temperature to leave pores in the materials. Organic framework replication method is to use the porous coral with similar cancellous bone structures as artificial bone. Microspheres sintering method is to add the degradable polymer microspheres to the mould, heating to the temperature higher than the glass transition temperature, obtaining the porous support after the insulation, cooling and mold releasing. The main defects of the above methods are that the prepared material has a single type of pore structure, it is difficult to control the pore size and the connectivity in the existing processes, due to single pore structure the material is unable to satisfy multiple functional requirements. As it is difficult to control the pore size and the connectivity, it makes impossible to fully and accurately complete the required functions from the material.

In the recent decades, a new type of porous material—the multilevel porous material has become center of international research, due to its unique properties. The multilevel porous material has been already involved in many fields such as biotechnology, biomedicine, catalysis, separation, energy and optics. For example, researchers have designed biomaterials as multilevel pore structures, and have used different materials and different methods to prepare a variety of multilevel porous biomaterials Wang Jun introduced the preparation of porous niobium biomaterials by organic foam dipping method in his thesis "Foam Dipping Method far Preparing Porous Niobium Biomaterials and the Properties Thereof". First, configure the polyvinyl alcohol solution, use a polyurethane organic foam as a template to prepare a porous niobium body, and then sinter the porous niobium body to obtain porous niobium with two types of pores. The first type of pores have a pore diameter of 300-500 μm, and the pores of this type are connected with each other, and there are a large number of micropores in the cavity walls of the first-type pores. However, the distribution of the micropores in the multilevel pore material of this structure are arbitrary and has no connectivity and the pore size of the multilevel pore material prepared by the method is uncontrollable, and the pore distribution and connectivity are also not controllable.

P. Sepulveda et al. introduced a hydroxyapatite foam in In Vivo Evaluation of Hydroxyapatite Foams (Materials Research. Vol. 5, No. 3,253-256, 2002). The hydroxyapatite foam has macropores with diameter of 100 μm~500 μm, and micropores with diameter of 20 μm~300 μm penetrating to each other. The preparation method is foaming the ceramic suspension through gel filling, and performing heat preservation at 1350° C. for 2 hour structural arrangement of the macropores and the micropores of the prepared porous material is unreasonable, and the preparation method thereof is still unable to control the macropores and micropores effectively.

CN2012/10,185,031 discloses a method for preparing bionic artificial bone with multilevel (micro/nano) pore structure, and introduces a method achieved as follows: realizing a 150-800 μm gradient penetration of pores by sintering through a selective laser (with a spot diameter of micrometer scale), using the oxidative decomposition of a small amount of mixed polymer microspheres to form 10-100 μm random spherical pores during the sintering process, using the etching process to obtain irregular surface pores of tens of nanometers. Finally, to obtain a three-dimensional multilevel pore structure by the method. Due to the randomness and irregularity of the pore structure, the preparation method is unable to produce regular pores. The multilevel porous material of this structure still cannot satisfy the functional requirements of bionic artificial bone.

CN2014/10,337,365 'Macroscopic-microscopic-nanometer Structural Mechanics Adaptable Bone Prosthesis and Preparation Thereof' introduces a hone prosthesis. The bone prosthesis comprises a body with macroscopic porous metal structure, a body with microscopic porous structure and a nanofiber. The internal macroscopic pores have a size of 300-1500 microns, the macroscopic pores are in complete connection with each other, the microscopic porous structure body is located in the macroscopic porous metal structure body. The internal microscopic porous structure is uniform, and the pores are completely connected with each other, and the pore size is 50-250 microns. The pore walls of the micropores are composed of nanofibers; the preparation method is as follows: firstly, the macroscopic porous metal structure body is prepared by 3D printing technology, the biodegradable polymer material is then prepared to be a solution through an organic solvent, which is poured into the pores of the macroscopic porous metal structure body, and then is frozen, performing thermally induced phase separation. Similarly, the pore structure at all levels of the multilevel porous material of this kind of structure is unreasonable, the preparation method is unable to effectively control the size of the pores, unable to satisfy the functional requirements as a bone prosthesis.

SUMMARY OF THE INVENTION

The object of the present invention is to provide a porous material with a multilevel pore structure which is reasonable in structure and is able to satisfy Various functional requirements of the material.

Another object of the present invention is to provide a method for preparing a porous material with controllable pore structure and pore size.

The inventor has carefully analyzed the prior art and found some drawbacks of them: due to the single pore structure, the material can perform often single function and is unable to satisfy multiple functional requirements. The pore size is set unreasonably, and the connectivity is not sufficient, which makes the material unable to satisfy the functional requirements. For example, as a biological material, insufficient connectivity will not be conducive to infiltration and transmission of tissue fluid, failing to achieve the excretion of products of the protein degradation and metabolites. The hydroxyapatite foam prepared by P. Sepulveda et al used as a biomaterial the micropores with diameter of 20 μm~300 μm are in the same order of magnitude as the size of the cells, making it difficult for the cells to feel the stress when the material is stressed, resulting in stress shielding. In addition, the uniformity of the pores is poor causing the non-uniformity of the performance of the pores. Besides, in term of the preparation method, the prior art can not achieve the effective control of multilevel pore structure and connectivity. If the porous material uses multilevel pore structure, and the pore structure and the pore size at all levels are reasonably designed, the pore structure at each level has unique physical and chemical properties, and play their different functions to satisfy the requirements. Wherein the connectivity is good, and pores are uniformly distributed. Besides, there is an efficient method for preparing the above-mentioned material, which can sufficiently and accurately satisfy the functional requirements of the various materials The object of the present invention is realized by the following technical solutions.

A porous material includes a material body, the body is composed of pore cavities classified into different levels according to the pore size of the material and cavity walls surrounding to form the pore cavities. On the cavity walls, which are formed around the upper-level cavities in a three-dimensional-space, are provided with lower-level pore cavities. The pore cavities of the same level at all levels are connected to each other and the pore cavities among different levels are also connected with each other.

Preferably, in the above porous material, each level of the porous materials in the material body is a continuous structure body, so that each level of the porous material can exist as an independent porous material in the body to exert its unique function.

Further, in the above porous material, each level of porous material in the material body is a continuous structure body, and the maximum outer boundary of each level of porous material is equivalent to the space boundary of the entire material body. That is, each level of porous material can exist as an independent level of porous material in the body, and has its own physicochemical properties. Such a structure can make the physicochemical properties of the porous materials at all levels different, and has different physicochemical properties in the entire space of a relatively fixed material to satisfy various functional requirements better.

Preferably, in the above porous material, each level of the porous materials in the material body has its own physicochemical properties, so that each level of porous material can perform its own unique function respectively, and the whole material can satisfy various functional requirements.

Preferably, in the above porous material, the lower-level porous materials constitute the cavity walls of the upper-level pore cavities, so that the pore cavities can be layered hierarchically, the structure of the pore cavity and pore size can be reasonably arranged.

Preferably, in the above porous material, the cavity walls of the upper pore cavities are composed by compounding the porous material of some lower levels or each lower level, so that the material can satisfy specific functional requirements.

Preferably, in the porous material, the pores at all levels are uniformly distributed in the material body to provide uniform properties within the material body.

Preferably, in the porous material, the pore size of the pore cavities at the same level is highly concentrated in a specific size range, and further, the number of pores in a specific size range of the pores cavities at the same level accounts for more than 80% of the total number of the pores, which can make the porous material to satisfy the special needs of requiring a particular size of the cavity.

Preferably, the porous material is a material made of a metal or a nonmetal, or a composite material made of a metal and a nonmetal.

Preferably, the porous material is a material prepared from one or more of tantalum, niobium, titanium, titanium alloy, stainless steel, cobalt-based alloy, nickel, nickel alloy, magnesium or magnesium alloy.

Preferably, the porous material is a material made of a ceramic material, including one or more of a high siliceous silicate material, an aluminosilicate material, a diatomaceous earth, material, a pure carbonaceous material, a corundum or a diamond material.

Another object of the present invention is realized as follows: a method for preparing a porous material, includes the following steps:

(1) material preparation mixing the raw material powder with a pore-forming agent for preparing smallest-level pores of the porous material and formulating a slurry; uniformly filling the slurry into a polymer material support to form a green body and then drying and smashing to obtain mixed grains containing raw materials, a pore-forming agent and materials of polymer materials support;

(2) uniformly mixing the mixed grains obtained in the foregoing step with a pore-forming agent for preparing the upper-level pore cavities which are bigger than the smallest-level pores of the porous material to make a compact green body;

(3) sintering the compact green body in vacuum; the sintered body is subjected to conventional follow-up treatment according to the raw material process of the porous material to obtain the porous material.

After the vacuum sintering of the compact green body, two pore-forming agents materials are volatilized to form two-level pores, thereby preparing multilevel porous materials. The smashed polymer material is volatilized and interconnection of the material is enhanced.

Preferably, in the preparation method of the porous material, uniformly mixing the mixed grains with a pore-forming agent for preparing cavities of the level which are one level higher than the smallest-level cavities of the porous material, and uniformly pouring them into the polymer material support before preparing the compact green body, the pore size of the polymer material support is greater than the particle size of the mixed grains and the particle size of the pore-forming agent, the strut is used as the pore-forming agent for the cavities which are two level higher than the smallest-level cavities. In this way after vacuum sintering, a multilevel porous material with three-level pores can be prepared. Similarly, the porous materials containing more levels can be prepared.

Preferably, in the preparation of the porous material, the pore cavities of the polymer material support having a pore size which is larger than the particle size of the mixed grains and the pore size of the pore-forming agent is three-dimensionally interconnected, thereby to prepare a three-dimensionally interconnected multilevel porous material.

The advantages of the present invention are as follows.

(1) The present invention provides a porous material having a multilevel pore structure, which is capable of satisfying various functional requirements.

(2) The porous material is three-dimensionally interconnected, including three-dimensional interconnection of pores within each level, and the pores at different levels are also three-dimensionally interconnected to each other, the connectivity thereof is good, the pores of each level are uniformly distributed, fully satisfying the functional requirements of the materials.

(3) The porous material ensures the overall uniformity the properties of the material.

(4) Due to the uniform distribution of pores at all levels of the porous material, the properties of the porous material are uniform and stable.

(5) In the porous material, the pore sizes of the pore cavities at the same level are highly concentrated in a specific size range, which enables it to satisfy the special requirement of having a pore cavity with a specific size, for example, to be used as biological materials, the pore cavities of a certain level can be designed to a specific size to satisfy the adhesion and residence requirements of cells; to be used for filtration, it can filter particles of a specific size range.

(6) The present invention provides a porous material preparation method, capable of preparing a multilevel pore structure, which can effectively control the pore size and connectivity, the method is simple, easy to realize, the parameters thereof are easy to be controlled and adjusted.

BRIEF DESCRIPTION OF THE DRAWING

The present invention will be further described with reference to the accompanying drawings and embodiments.

DETAILED DESCRIPTION OF THE INVENTION

Specific embodiments of the present invention are described below with reference to the accompanying drawings. The embodiments are given based on the technical solutions of the present invention, and the specific implementation manners and specific operation procedures are given. However, the protection scope of the present invention is not limited to the following embodiments.

Figure 1:
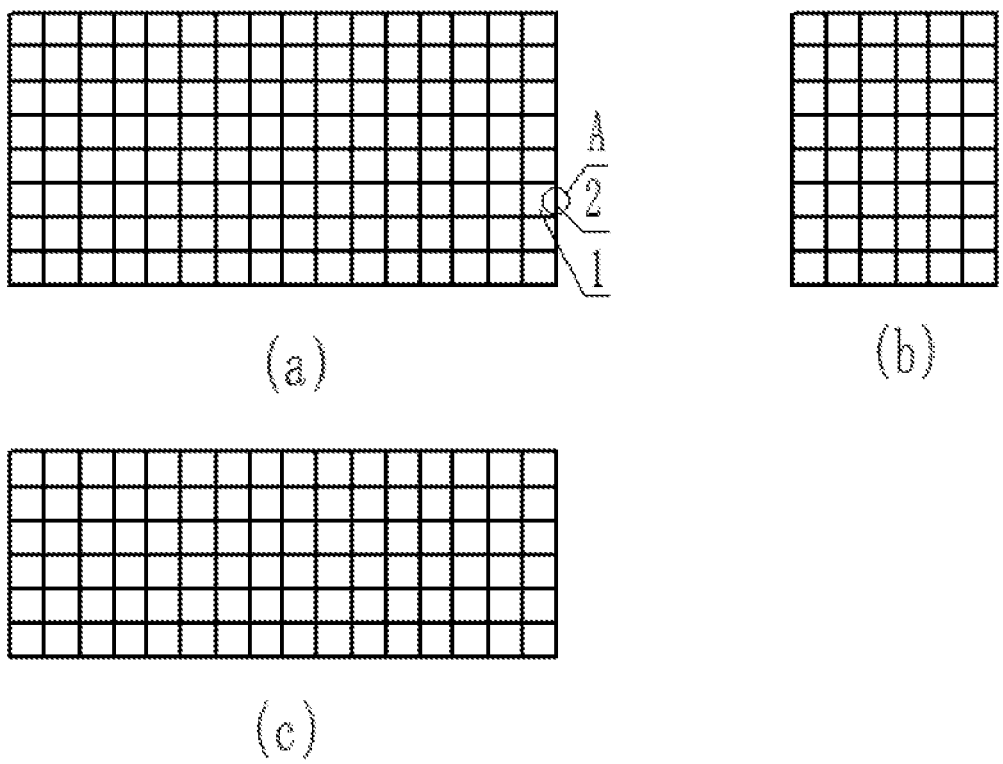
FIG. 1 is a schematic view of the porous material of the present invention, (a) is a front view, (b) is a left view, (c) is a plan view.
Figure 2:
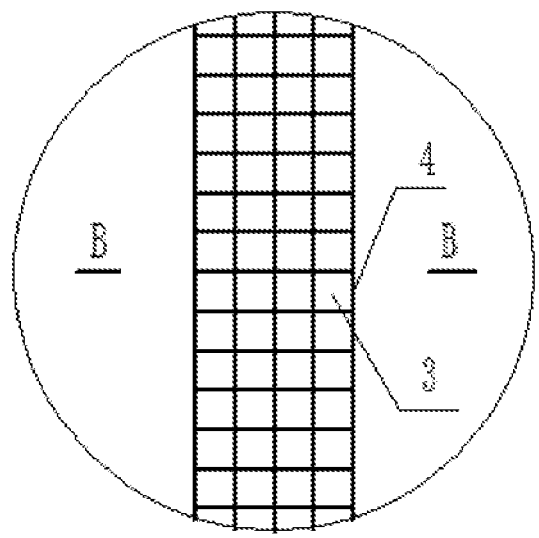
FIG. 2 is a partial enlarged view of A in FIG. 1.
Figure 3:
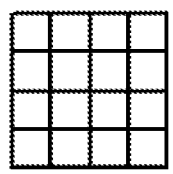
FIG. 3 is a B-B sectional view of FIG. 2.

FIG. 1 shows a three-dimensionally interconnected porous material, wherein, 1 is the pore cavity and 2 is the cavity wall. It can be seen from FIG. 2 that the cavity wall 2 of the cavity 1 is formed by the smaller pore cavities 3 (the next level pores) and the cavity wall 4 surrounding the pore cavity 3. Combining the enlarged view of the cavity wall 2 in FIG. 2 with the B-B sectional view in FIG. 3, it can be seen that the pore cavity 3 is three-dimensionally interconnected, and the pores at two levels are also three-dimensionally interconnected.

Similarly, the porous material with more than three levels of multilevel pore structure can be formed.

The porous material of each level containing pore cavity 1 and pore cavity 3 in the material body is a continuous structure body.

The maximum boundary of each level of porous material containing pore cavities 1, and pore cavities 3 is equivalent to the space boundary of the entire material body.

The porous material of each level containing pore cavities 1 and pore cavities 3 in the material body has its own physicochemical properties.

Pore cavities 1, pore cavities 3 and the pores at all levels are uniformly distributed in the material body.

In the figure, the number of pore cavities 1 and pore cavities 3 accounts for 100% of the total number of pore cavities in this level.

The porous material may be made of metal or non-metal, or a composite material made ref metal and non-metal.

The embodiments of the present invention are given below in detail.

Embodiment 1

The porous material of the present embodiment is porous tantalum and has three-level pores, wherein the cavity walls of the first-level pore cavities, which are uniformly distributed and interconnected, are provided with the uniformly distributed and interconnected second-level pore cavities, the cavity walls of the second-level pore cavities are provided with uniformly distributed and interconnected third-level pore cavities; and the pore cavities at different levels are also connected with each other, forming a three-dimensional interconnection. The porous material of each level is a continuous structure body, the maximum boundary of the porous material of each level equivalent to the space boundary of the material body.

The preparation method is as follow.

(1) The preparation of materials.

Use tantalum powder with particle size of 1-10 μm as raw material and starch with particle size of 300 nm-700 nm as a pore-forming agent for the smallest-level pore cavities of porous material, use stearic acid with particle size of 300 nm-700 nm as a binder, and formulate a slurry by tantalum powder, starch, stearic acid and distilled water in a volume ratio of 3:1:1:10.

Use a polyester foam having a pore size of 500-800 µm, and uniformly fill the slurry therein by a foam dipping method to form a green body and get dried, and then get smashed to obtain the mixed grains with particle size of 40-80 µm containing raw materials, a pore-forming agent and a polyester foam.

(2) Uniformly mix the mixed grains with ethyl cellulose having a particle size of 40-80 µm in a volume ratio of 3:1, then uniformly pour into a three-dimensional interconnected polyester foam having a strut diameter of 200-400 µm and a pore diameter of 340-440 µm. Then put the polyester foam into a closed mould to press into a compact green body.

(3) Perform vacuum sintering to the compact green body; perform the conventional follow-up heating treatment to sintered green body according to the tantalum material process to obtain the three-level porous tantalum.

Using the section direct observation method to respectively prepare planes in the three-dimensional direction of the sample and observe the pores through an electron microscope. Image was digitally processed and the average of the three surfaces was taken. The observation results showed that: the pore size of the first-level pore cavities was 150 µm~360 µm, the pore size of the third-level pore cavities was 200 nm~600 nm, and the pore size of the second-level pore cavities was 30~70 µm. Wherein, in the first-level pore cavities, pore size of 270±30 µm account for 87%, in the second-level pore cavities, pore size of 50±10 µm account for 85%, in the third-level pore cavities, pore size of 450±60 nm account for 82%. Respectively comparing the total pore area of each level with the total area of the sample, the porosity of the first-level pore cavities was 64%, the porosity of the second-level pore cavities was 10%, the porosity of the third-level pore cavities was 6%.

According to GBT/7314-2005 "Metallic materials-Compression testing at ambient temperature", the material of this embodiment has a compressive strength of 36 MPa and an elastic modulus of 1.15 GPa, which is very close to the elastic modulus of human cancellous bone.

In the porous tantalum, the porous material of each level has its own structure and properties, for example, the porous material of each level has a unique pore size, compressive strength, elastic modulus, etc. Thereby each level can satisfy different functional requirements, it can be used as biological regeneration material. The size of the first-level pore cavities is used to satisfy the growing needs of blood vessels and other tissues; the pore cavities of second-level are used for inhabited of variety of cells; the pore cavities of third-level are used for satisfying the needs of adhesion and differentiation of cells. Particularly, the multilevel pore structure thereof makes elastic modulus of the cavity wall different horn that of the raw material itself, but to reduce the elastic modulus of the cavity walls. The existence of the third-level pore cavities enable the cells to inhabit on the cavity walls of the second-level pore cavities to truly sense the stress when the material is stressed to promote the cell division, thereby creating a fundamental condition for cell division and avoiding stress shielding. Besides, the connectivity of the pore cavities is good, pores of each level are mutually interconnected and pores at different levels are also mutually interconnected, which can hilly satisfy the infiltration and transmission of tissue fluid, achieving the excretion of products of the protein degradation and metabolites, thus it is a real biological regeneration material.

Embodiment 2

The porous material of the present embodiment is porous silicon carbide with two-levels pores, wherein the cavity walls of the first-level pore cavities, which are uniformly distributed and interconnected, are provided with uniformly distributed and interconnected second-level pore cavities, and the pores of two levels are also interconnected with each other, forming a three-dimensional interconnection.

The preparation method is as follow.

(1) The preparation of materials.

Use silicon carbide powder with particle size of 1-10 µm and urea with particle size of 35-70 µm as a pore-forming agent for the smallest-level cavities of the porous material, uniformly mix them, use 35-70 µm starch as a binder, formulate a slurry by silicon carbide powder, urea, starch and distilled water in a volume ratio of 4:1.5:1:12.

Uniformly fill the slurry into a polyester foam having a pore diameter of 600-900 µm by foam dipping method to form a green body and get it dried, and then get smashed to obtain the mixed grains with particle size of 35-70 µm containing a raw material, a pore-forming agent and a polyester foam.

(2) Uniformly mix the mixed grains with the methyl cellulose having particle size of 700-950 µm in a volume ratio of 4:1, put them into a closed mould to press into a compact green body.

(3) Perform the vacuum sintering to the compact green body; the sintered body is subjected to conventional follow-up treatment according to the silicon carbide process to obtain the porous silicon carbide with two levels of pores.

According to the method of Embodiment 1, the pore diameter of the first-level pore cavities is 630-860 µm, the pore diameter of second-level pore cavities is 25-60 µm. Wherein, the pore cavities with pore diameter of 710±30 µm account for 89% of the first-level pore cavities, and the pore cavities with pore diameter of 45±10 µm account for 83% of the second-level pore cavities. The porosity of the first-level pore cavities is 51% and the porosity of the second-level pore cavities is 12%.

The material can be used for separation of solids and liquids, achieving hierarchical filtration, pores of two levels filter particles with different sizes respectively, to avoid the accumulation of particles in one side of the material to achieve efficient separation.

Embodiment 3

The porous material in this embodiment is porous niobium and has three levels of pores. Wherein, the cavity walls of the uniformly distributed and interconnected first-level pore cavities are provided with the uniformly distributed and interconnected second-level pore cavities. The cavity walls of the second-level pore cavities are provided with uniformly distributed and interconnected third-level pore cavities; and the cavities of each levels are also interconnected, forming a three-dimensional interconnection. The porous material of each level is a continuous structure body, the porous material of each level fully occupies the inside space of the entire material body.

The preparation method is as follow.

(1) The preparation of materials.

Use niobium powder with particle size of 1-10 µm as raw material, use methylcellulose with particle size of 200-500 nm as a pore-forming agent for the smallest-level pore cavities of porous material, use polystyrene with particle size of 200-500 nm as a binder, formulate a slurry by niobium powder, methylcellulose, polystyrene and distilled water in a volume ratio of 4:1:1:12.

Use a polyester foam with a pore diameter of 500-800 µm, the slurry is uniformly filled by the foam dipping method to form a green body and get it dried, and then get smashed to obtain mixed grains with particle size of 30-70 µm containing raw materials, a pore-forming agent and a polyester foam.

(2) Uniformly mix the mixed grains and ethylcellulose with particle size of 30-70 µm in a volume ratio of 5:2, after that, uniformly pour them into a three-dimensional interconnected polyester foam with a strut diameter of 500-650 µm and a pore size of 660-870 µm. Then put the polyester foam into a closed mould to press into a compact green body.

(3) Perform vacuum sintering to the compact green body; the sintered body is subjected to conventional follow-up heating treatment according to the niobium material process to obtain porous niobium with three levels of pores.

According to the method of Embodiment 1, the pore size of the first-level pore cavities is 450-560 µm, the pore size of the third-level pore cavities is 150-400 nm, and the pore size of the second-level pore cavities is 25-60 µm. Wherein, the pore cavities with pore size of 510±50 µm account for 85% of the first-level pore cavities, the pore cavities with pore size of 45±10 µm account for 82% of the second-level pore cavities, the pore cavities with pore size of 270±40 nm account for 88% of the third-level pore cavities. The porosity of the first-level pore cavities is 61%, the porosity of the second-level pore cavities is 9%, and the porosity of the third-level pore cavities is 5%.

Test according to the standard of Embodiment 1, the compressive strength of the material of this embodiment is 24 MPa, the elastic modulus is 0.62 GPa, which is very close to the elastic modulus of human cancellous bone and can be used as the bone implant materials. Similar to the embodiment 1, it is a real biological regeneration material.

What is claimed is:

1. A porous material, comprising:
    a material body, wherein the material body is composed of pore cavities, the pore cavities comprising first-level pore cavities, second-level pore cavities and third-level pore cavities; and
    cavity walls surrounding the pore cavities;
    wherein
    the second-level pore cavities are arranged on the cavity walls of the first-level pore cavities and the third-level pore cavities are arranged on the cavity walls of the second-level pore cavities;
    the pore cavities of a same level at all levels are connected to each other, the pore cavities among different levels are connected with each other, and the pore cavities of each level are uniformly distributed in the material body;
    the porous material is a porous metal material, a porous non-metal material or a composite material made of the porous metal material and the porous non-metal material;
    the porous metal material is one or more selected from the group consisting of tantalum, niobium, titanium, titanium alloy, stainless steel, cobalt based alloy, nickel, nickel alloy, magnesium and magnesium alloy;
    the porous non-metal material is one or more selected from the group consisting of ceramic materials, aluminosilicate materials, diatomaceous earth materials, and corundum;
    wherein more than 80% of pore sizes of the first-level pore cavities are between 150 µm and 360 µm, more than 80% of pore sizes of the second-level pore cavities are between 30 µm and 70 µm, and more than 80% of pore sizes of the third-level pore cavities are between 200 nm and 600 nm.

2. The porous material according to claim 1, wherein the each level of the porous material is a continuous structure body in the material body.

3. The porous material according to claim 2, wherein a maximum outer boundary of the each level of the porous material is equivalent to a space boundary of the entire material body.

4. The porous material according to claim 1, wherein the each level of the porous material in the material body has its own physicochemical properties.

\* \* \* \* \*